United States Patent
Melzig et al.

(10) Patent No.: US 7,892,296 B2
(45) Date of Patent: Feb. 22, 2011

(54) PHOTOCHROMIC BENZOPYRANS

(75) Inventors: Manfred Melzig, Wessling (DE); Yven Rohlfing, Munich (DE); Udo Weigand, Munich (DE)

(73) Assignee: Rodenstock GmbH, Munich (DE)

( * ) Notice: Subject to any disclaimer, the term of this patent is extended or adjusted under 35 U.S.C. 154(b) by 0 days.

(21) Appl. No.: 12/738,124

(22) PCT Filed: Nov. 25, 2008

(86) PCT No.: PCT/EP2008/009991

§ 371 (c)(1),
(2), (4) Date: Apr. 15, 2010

(87) PCT Pub. No.: WO2009/068247

PCT Pub. Date: Jun. 4, 2009

(65) Prior Publication Data

US 2010/0243971 A1   Sep. 30, 2010

(30) Foreign Application Priority Data

Nov. 26, 2007 (DE) .................. 10 2007 057 108

(51) Int. Cl.
*C07D 311/00* (2006.01)
(52) U.S. Cl. .............................. 8/507; 8/506; 549/200; 549/382
(58) Field of Classification Search .......... 8/506, 8/507; 549/200, 382
See application file for complete search history.

(56) References Cited

U.S. PATENT DOCUMENTS

| | | | |
|---|---|---|---|
| 3,567,605 A | 3/1971 | Becker | |
| 5,645,767 A | 7/1997 | Van Gemert | |
| 5,698,141 A | 12/1997 | Kumar | |
| 5,723,072 A | 3/1998 | Kumar | |
| 5,955,520 A | 9/1999 | Heller et al. | |
| 6,018,059 A | 1/2000 | Chan | |
| 6,022,495 A | 2/2000 | Kumar | |
| 6,146,554 A | 11/2000 | Melzig et al. | |
| 6,379,591 B1 | 4/2002 | Breyne | |
| 6,426,023 B1 | 7/2002 | Breyne et al. | |
| 6,506,538 B1 * | 1/2003 | Breyne et al. | 430/270.17 |
| 6,558,583 B2 | 5/2003 | Breyne et al. | |
| 2004/0094753 A1 | 5/2004 | Izumi et al. | |
| 2008/0262248 A1 | 10/2008 | Weigand et al. | |

FOREIGN PATENT DOCUMENTS

JP   2000344762   12/2000

OTHER PUBLICATIONS

PCT/EP2008/009991; PCT International Search Report dated Feb. 13, 2009.
PCT/EP2008/009991; International Preliminary Report on Patentability dated Jul. 27, 2010.

* cited by examiner

*Primary Examiner*—Lorna M Douyon
*Assistant Examiner*—Amina Khan
(74) *Attorney, Agent, or Firm*—Renner, Otto, Boisselle & Sklar, LLP

(57) ABSTRACT

The present invention relates to photochromic benzopyrans and to the use thereof in plastics of all kinds, especially for ophthalmic purposes. The inventive compounds are photochromic benzopyran compounds in which a polycyclic aromatic is joined to the 5 and 6 positions of a benzopyran, where the bond in the 6 position is direct and the bond in the 5 position is via a mono- or diatomic bridge.

14 Claims, 2 Drawing Sheets

PHOTOCHROMIC BENZOPYRANS

The present application is a U.S. National Stage Application based on and claiming priority under 35 U.S.C. §371 to International Application No. PCT/EP2008/009991, filed Nov. 25, 2008, the entirety of which is hereby incorporated by reference.

The present invention relates to photochromic benzopyrans and to the use thereof in plastics of all kinds, especially for ophthalmic purposes. The inventive compounds are photochromic benzopyran compounds in which a polycyclic aromatic is joined to the 5 and 6 positions of a benzopyran, where the bond in the 6 position is direct and the bond in the 5 position is via a mono- or diatomic bridge.

There has long been knowledge of various dye classes which, on irradiation with light of particular wavelengths, especially solar rays, reversibly change color. This is because these dye molecules are converted by light energy to an excited state, which they leave again in the event of interruption of the energy supply and revert to their starting state. These photochromic dyes include various pyran systems which have already been described in the prior art with different base systems and substituents.

Pyrans, specifically naphthopyrans and larger ring systems derived from these, are currently the class of photochromic compounds which has been the subject of the most work. Even though a patent was first filed as early as 1966 (U.S. Pat. No. 3,567,605), it was not until the 1990s that compounds which appeared suitable for use in spectacle lenses were developed. Suitable classes of pyran compounds are, for example, the 2,2-diaryl-2H-naphtho[1,2-b]pyrans or the 3,3-diaryl-3H-naphtho-[2,1-b]pyrans, which, in excited form, exhibit various colors, such as yellow, orange or red-orange.

A further class of photochromic compounds of interest is that of more highly fused pyrans which absorb at a longer wavelength owing to their larger ring system and give red, violet and blue hues. These may be systems derived either from the 2H-naphtho[1,2-b]pyrans or the 3H-naphtho[2,1-b] pyrans, which originate from the particular naphthopyran systems by fusion on the f side.

Diarylchromenes, especially naphthopyrans or hetero-cyclically fused benzopyrans, which are 6-substituted on the benzopyran by a phenyl ring or more generally an aromatic or heteroaromatic ring which is additionally bridged via the 5 position of the benzopyran via at least one carbon atom, oxygen atom or nitrogen atom, are currently the most promising photochromic compounds.

When this bridge is generated only via one atom, the result is a five-membered ring fused to the benzopyran. Examples of one carbon atom can be found in U.S. Pat. No. 5,645,767, U.S. Pat. No. 5,723,072 and U.S. Pat. No. 5,955,520, and examples of one oxygen atom in U.S. Pat. No. 6,018,059.

In U.S. Pat. No. 5,723,072, an un-, mono- or disubstituted heterocyclic ring may additionally be fused to this base system on the g, h, i, n, o or p side of the indenonaphthopyran. Accordingly, indeno[1,2-f]naphtho[1,2-b]-pyrans with a very wide range of variation of possible substituents are disclosed.

WO 96/14596, WO 99/15518, U.S. Pat. No. 5,645,767, WO 98/32037 and U.S. Pat. No. 5,698,141 disclose photochromic indenofused naphthopyran dyes derived from 2H-naphtho[1,2-b]pyran, the compositions comprising them and a process for preparation thereof. In U.S. Pat. No. 5,698,141, an un-, mono- or disubstituted heterocyclic ring may additionally be fused to this base system on the g, h, i, n, o or p side of the indenonaphthopyran. The substituent list, which is very extensive in each case, also includes quite specific spiro compounds, more particularly those systems with a spiro heterocyclic group in which, including the spiro atom at the 13 position of the base system, a 5- to 8-membered ring which always contains two oxygen atoms is present. A further embodiment of the spiro ring can be found in Japanese application 344762/2000.

When this bridge is generated via two atoms, the result is a fused six-membered ring with various options solely for C, O and N. Compounds with C=O and N—R (lactam bridge) are described in U.S. Pat. No. 6,379,591. Compounds with an unsubstituted $CH_2$—$CH_2$ bridge and a fused heterocycle in the 7,8 position of the parent benzopyran are disclosed in U.S. Pat. No. 6,426,023.

U.S. Pat. No. 6,506,538 describes the carbocyclic analog compounds in which the hydrogen atoms in the bridge may be replaced by OH, ($C_1$-$C_6$)-alkoxy, or two hydrogen atoms on one carbon atom may be replaced by =O. Alternatively, one of the carbon atoms in the two-membered bridge may also be replaced by oxygen. These compounds among others are described in WO 00/02884.

When this bridge is generated by three atoms, the result is a fused 7-membered ring with very many possible variations through insertion of heteroatoms. Compounds with a $CH_2$—$CH_2$—$CH_2$ bridge are described in U.S. Pat. No. 6,558,583. Here too, the hydrogen atoms in the bridge may be replaced by OH, ($C_1$-$C_6$)-alkyl or ($C_1$-$C_6$)-alkoxy, or two hydrogen atoms on one carbon atom may be replaced by =O. Given the same substitution pattern, they absorb at a shorter wavelength than the fused 6-membered rings.

US 2004/0094753 describes both compounds with a diatomic and with a triatomic bridge. The diatomic (carbon) bridge is additionally fused to a carbo- or a heterocycle. The triatomic bridge contains three carbon atoms or two carbon atoms and one oxygen atom with no additional fusion. Both rings may bear various substituents.

The different photochromic dyes available in the prior art, however, have disadvantages which, when used in sunglasses, significantly impair the wear comfort of the wearer. Firstly, the dyes have insufficiently long-wave absorption in the excited state and in the unexcited state. Secondly, there is frequently too high a thermal sensitivity of the darkening, and lightening may at the same time be too slow. Furthermore, the dyes available in the prior art often have an inadequate lifetime and hence allow only a short service life of the sunglasses. The latter becomes perceptible in rapidly declining performance and/or significant yellowing.

It is therefore an object of the present invention to provide further photochromic compounds which should feature the combination of a long-wave absorption maximum of the closed form with a steep edge to the visible wavelength range, high darkening performance, very rapid lightening reaction and very good light stability.

This object is achieved by the articles characterized in the claims.

More particularly, photochromic benzopyrans with the general formula (I) are provided:

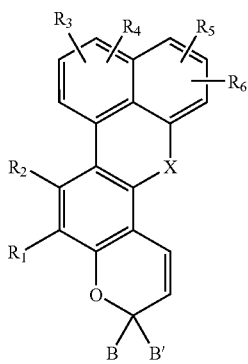

(I)

in which the $R_1$, $R_2$, $R_3$, $R_4$, $R_5$ and $R_6$ radicals are each independently a substituent selected from the group α consisting of a hydrogen atom, a $(C_1-C_6)$-alkyl radical, a $(C_1-C_6)$-thioalkyl radical, a $(C_3-C_7)$-cycloalkyl radical which may have one or more heteroatoms, for example O or S, a $(C_1-C_6)$-alkoxy radical, a hydroxyl group, a trifluoromethyl group, bromine, chlorine, fluorine, an un-, mono- or disubstituted phenyl, phenoxy, benzyl, benzyloxy, naphthyl or naphthoxy radical, where the substituents may in turn be selected from the group α; or the $R_1$ and $R_2$ or $R_3$ and $R_4$ (when in the ortho position to one another) or $R_4$ and $R_5$ (when each in the peri position) or $R_5$ and $R_6$ (when in the ortho position to one another) radicals each independently form an -A-$(CH_2)_k$-D- or -A-$(C(CH_8)_2)_k$-D- group bonded to the aromatic ring, where k=1 or 2, where A and D are each independently selected from oxygen, sulfur, $CH_2$, $C(CH_8)_2$ or $C(C_8H_8)_2$, and where a benzo ring may in turn be fused to this -A-$(CH_2)_k$-D- group; or the $R_1$ and $R_2$ or $R_3$ and $R_4$ or $R_5$ and $R_6$ radicals are each independently an unsubstituted, mono- or disubstituted, fused benzo, pyrido, naphtho, benzofuro or benzothieno ring, the substituents of which may be selected from the group α;

X is a mono- or diatomic bridge, where X in the case of a monoatomic bridge is selected from O and $CR_7R_8$, where the $R_7$ and $R_8$ radicals are each independently selected from the group α, or including the spiro carbon atom are a 3- to 8-membered carbo- or heteromonocyclic ring which optionally bears one or more substituents from the group α and to which one to three aromatic or heteroaromatic ring systems may be fused, where the ring system(s) is/are independently selected from the group β consisting of benzene, naphthalene, phenanthrene, pyridine, quinoline, furan, thiophene, pyrrole, benzofuran, benzothiophene, indole and carbazole, which may in turn be substituted by one or more substituents selected from the group α, or including the spiro carbon atom are a 7- to 12-membered carbobicyclic ring or a 7- to 12-membered carbotricyclic ring which may in turn have one, two, three or four substituents selected from the group α, or where X, in the case of a diatomic bridge, is formed from the —Y—Z— moiety, where Y and Z are each independently selected from O, $CR_9R_{10}$ and $CR_{11}R_{12}$, where the $R_9$ to $R_{12}$ radicals are each independently selected from the group α, or $R_9$ and $R_{10}$ or $R_{11}$ and $R_{12}$ including the spiro carbon atom are a 3- to 8-membered carbo- or heteromonocyclic ring which optionally bears one or more substituents from the group α and to which one to three aromatic or heteroaromatic ring systems may be fused, where the ring system(s) is/are independently selected from the group β consisting of benzene, naphthalene, phenanthrene, pyridine, quinoline, furan, thiophene, pyrrole, benzofuran, benzothiophene, indole and carbazole, which may in turn be substituted by one or more substituents selected from the group α, or $R_9$ and $R_{10}$ or $R_{11}$ and $R_{12}$ including the spiro carbon atom are a 7- to 12-membered, carbobicyclic ring or a 7- to 12-membered carbotricyclic ring which may in turn have one, two, three or four substituents selected from the group α;

or Y and Z are joined to one another via a radical in each case to form a 4- to 8-membered carbocyclic ring, where the ring members may each independently bear one or more substituents selected from the group α;

with the proviso that, in the case of a diatomic bridge, only a maximum of one carbobicyclic or carbotricyclic system is present, and that Y and Z are not both O; and B and B' are each independently selected from one of the following groups a), b) and c):

a) mono-, di- and trisubstituted aryl radicals, where the aryl radical is phenyl, naphthyl or phenanthryl;

b) unsubstituted, mono- and disubstituted heteroaryl radicals, where the heteroaryl radical is pyridyl, furanyl, benzofuranyl, thienyl, benzothienyl, 1,2,3,4-tetrahydrocarbazolyl or julolidinyl;

where the substituents of the aryl or heteroaryl radicals in a) and b) are those selected from the above-defined group α or from the group χ consisting of hydroxyl, 2-phenylethenyl un-, mono- or disubstituted on the phenyl ring, (phenylimino)methylene un-, mono- or disubstituted on the phenyl ring, (phenylmethylene)imino un-, mono- or disubstituted on the phenyl ring, amino, mono-$(C_1-C_6)$-alkylamino, di-$(C_1-C_6)$-alkylamino, mono- and diphenylamino un-, mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, un-, mono- or disubstituted phenothiazinyl, un-, mono- or disubstituted phenoxazinyl, un-, mono- or disubstituted 1,2,3,4-tetrahydroquinolinyl, un-, mono- or disubstituted 2,3-dihydro-1,4-benzoxazinyl, un-, mono- or disubstituted 1,2,3,4-tetrahydroisoquinolinyl, un-, mono- or disubstituted phenazinyl, un-, mono- or disubstituted carbazolyl, un-, mono- or disubstituted 1,2,3,4-tetrahydrocarbazolyl and un-, mono- or disubstituted 10,11-dihydrodibenzo[b,f]azepinyl, where the substituent(s) may each independently in turn be selected from $(C_1-C_6)$-alkyl, $(C_1-C_6)$-alkoxy, bromine, chlorine and fluorine;

or where two directly adjacent substituents are a U—$(CV_2)_p$—W— moiety where p=1, 2 or 3, V may be hydrogen, $CH_3$ or $C_6H_5$, and U and W may each independently be oxygen, sulfur, N—$(C_1-C_6)$-alkyl, N—$C_6H_5$, $CH_2$, $C(CH_3)_2$ or $C(C_6H_5)_2$, where two or more adjacent carbon atoms in this U—$(CV_2)_p$—W— moiety may each independently also be part of a benzo ring system fused thereto, which may in each case in turn have one or more substituents selected from the group α or the group χ;

or c) B and B' together with the adjacent carbon atom of the pyran ring form an un-, mono- or disubstituted 9,10-dihydroanthracene, fluorene, thioxanthene, xanthene, benzo[b]fluorene, 5H-dibenzo[a,d]cycloheptene or dibenzosuberone radical, or a saturated hydrocarbon radical which is $(C_3-C_{12})$-spiromonocyclic, $(C_7-C_{12})$-spirobicyclic or $(C_7$-

$C_{12}$)-spirotricyclic, where the substituents of the unsaturated cycles may each independently be selected from the group α or the group χ.

The inventive photochromic compounds derived from benzopyrans, in which a polycyclic aromatic is joined to the 5 and 6 positions of a benzopyran, where the bond in the 6 position is direct and the bond in the 5 position is via a mono- or diatomic bridge, are notable for very good lifetime and high lightening speed. The inventive compounds exhibit a significantly longer-wave absorption maximum compared to those without such an attachment of a polycyclic aromatic to the 5 and 6 positions. The inventive compounds feature a balance of long-wave absorption maximum, high darkening performance, very fast lightening reaction and very good light stability. The increased molar absorption in the short-wave range of visible light around 400 nm should be particularly emphasized.

Figure 1:
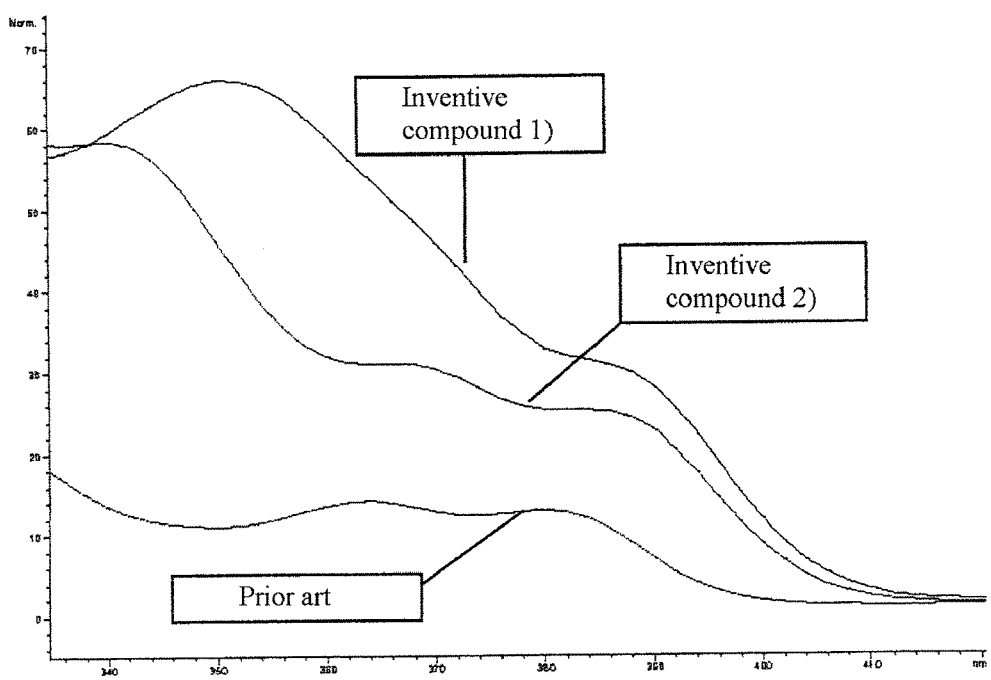
FIG. 1: Absorption spectra of the inventive compound

Preferred photochromic benzopyrans according to the present invention have the following general formulae (II) and (III):

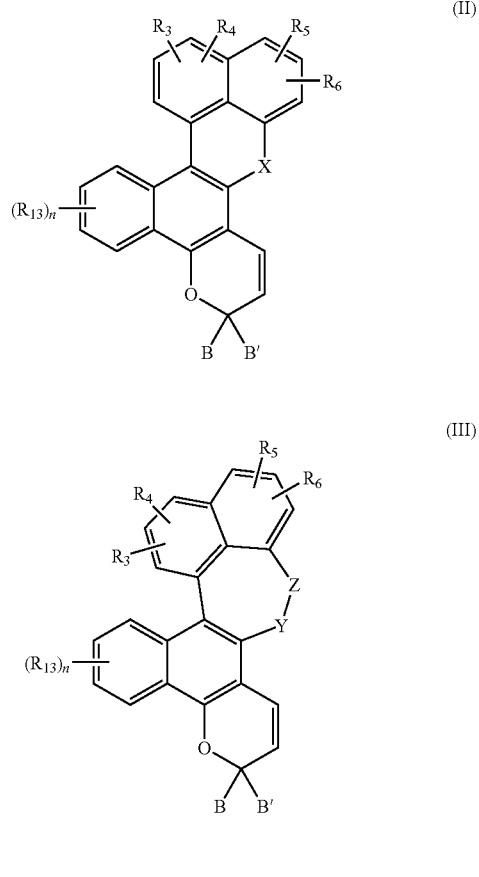

in which X is O or $CR_7R_8$, Y and Z are each as defined above, and B, B', $R_3$, $R_4$, $R_5$, $R_6$, $R_7$ and $R_8$ are each as defined above, $R_{13}$ is selected from the group a and n is 0, 1, 2, 3 or 4.

When B or B' is a saturated hydrocarbon radical which is $C_3$-$C_{12}$-spiromonocyclic, $C_7$-$C_{12}$-spirobicyclic or $C_7$-$C_{12}$-spirotricyclic, $C_3$-$C_{12}$-spiromonocyclic is understood to mean a 3- to 12-membered ring as familiar to the person skilled in the art. $C_7$-$C_{12}$-Spirobicyclic systems are also well known to a person skilled in the art. Examples here in turn include norbornane, norbornene, 2,5-norbornadiene, norcarane and pinane. An illustrative $C_7$-$C_{12}$-spirotricyclic system is adamantane.

In a further preferred embodiment, the B and B' radicals are each independently selected from group a) as defined above.

The substituents of the group χ which have nitrogen atoms or bear amine groups are bonded via the latter to the phenyl, naphthyl or phenanthryl radical of group a).

With regard to the substituents of the group χ which may be bonded to the phenyl, naphthyl or phenanthryl radical of group a) or the B or B' radicals, when two or more adjacent carbon atoms of this U—$(CV_2)_p$—W— moiety may each independently be part of a benzo ring system fused thereto, this means that the two methylene carbon atoms (—$CH_2$—$CH_2$—) may then become part of a fused ring system. When, for example, two or there benzo rings are fused, it is possible, for example, for the following structural units as shown below to be present:

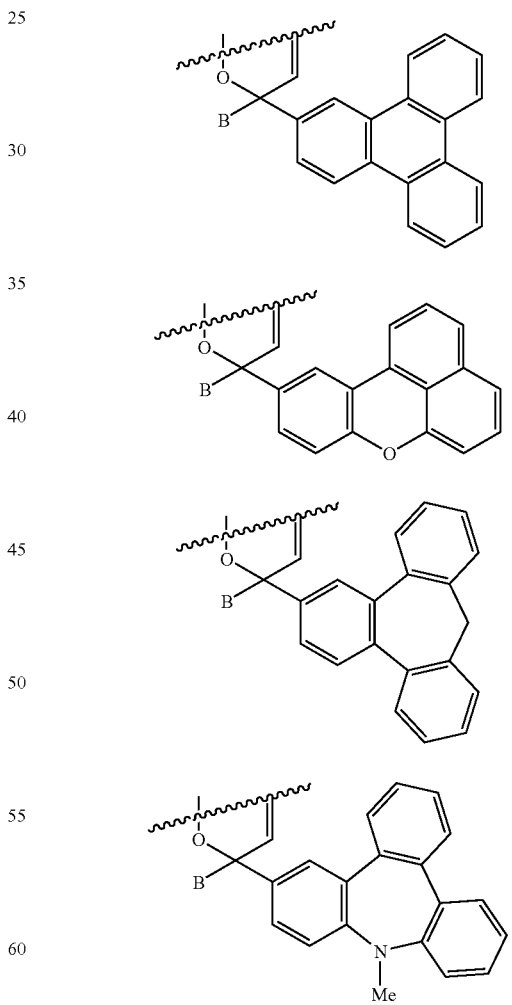

It will be appreciated, however, that it is also possible for only one benzo ring fused via two adjacent carbon atoms of this U—$(CV_2)_p$—W— moiety to be present.

When Y and Z in the above formulae (I) and (III) are joined to one another via a radical in each case to form a 4- to 8-membered carbocyclic ring, it is possible, for example, for compounds of the formula (IV) as shown below to be present, in which B, B', $R_3$, $R_4$, $R_5$, $R_6$, $R_7$ and $R_8$ are each as defined above, $R_{13}$ and $R_{14}$ are each independently selected from the group α, and n is in each case independently 0, 1, 2, 3 or 4:

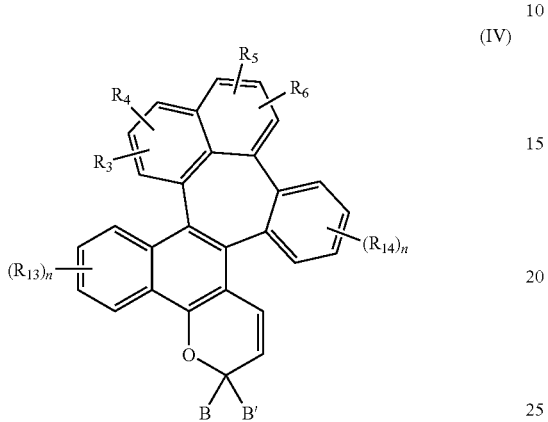

(IV)

In a preferred embodiment of the present invention, X in the formula (I) is a monoatomic bridge selected from O, $CH_2$ and $CMe_2$.

In another preferred embodiment of the present invention, X in the formula (I) is a diatomic bridge Y—Z selected from $CH_2$—$CH_2$, O—$CH_2$, $CH_2$—O and a benzo fusion.

Compared to the prior art (U.S. Pat. No. 6,506,538 or U.S. Pat. No. 6,558,583 for carbocyclic bridges and WO 00/02884 for bridges containing oxygen), in which a (substituted) benzene radical is bridged to the benzopyran base structure, the inventive compounds—given the same substituents B and B'—have a significantly longer-wave absorption band both in the unexcited and in the excited state. A longer-wave absorption in the unexcited state has two important advantages in the introduction of the photochromic dyes, for example, into plastic spectacle lenses. Firstly, the inventive compounds also react when, under unfavorable atmospheric conditions, only very long-wave UV sunlight (from 380 nm) is incident. It is evident from FIG. 1 that the inventive compounds in the unexcited form absorb significantly more intensely at wavelengths greater than 370 nm compared to prior art compounds. As a result, the inventive photochromic compounds, even under unfavorable conditions, exhibit very good darkening performance. Secondly, full UV protection up to 400 nm is achieved automatically as a result, since the inventive compounds completely absorb the incident UV light—there is no need to add UV absorbers in the production of sunglasses. This is an important advantage since added UV absorbers always absorb some of the incident light, such that lenses containing UV absorbers always darken to a lesser degree than without UV absorbers.

The structure of the inventive compounds shown in FIG. 1 and the longest-wave absorption maxima thereof in the excited form are shown in table 1 below (compared to the prior art from U.S. Pat. No. 6,558,583):

TABLE 1

Longest-wave absorption maxima in the excited state

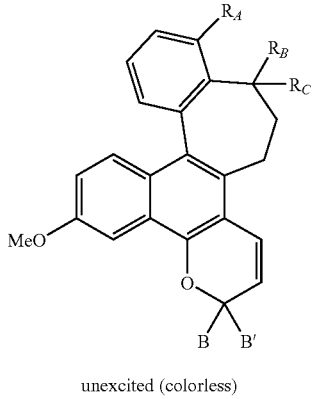

unexcited (colorless)

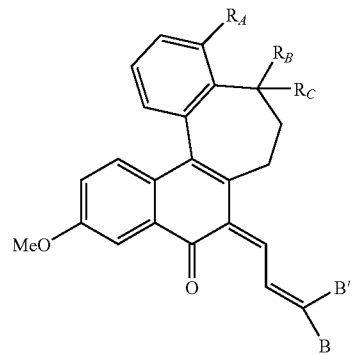

excited (colored)

A) Prior art (U.S. Pat. No. 6,558,583)

| $R_A$ | $R_B$ | $R_C$ | B | B' | $\lambda_{max}$ (excited) |
|---|---|---|---|---|---|
| H | H | H | Phenyl | 4-(N-Morpholinyl)phenyl | 555 nm |

B) Inventive compounds

| Comp. | $R_a$ | $R_B$ | $R_C$ | B | B' | $\lambda_{max}$ (excited) |
|---|---|---|---|---|---|---|
| 1) | Benzo fusion* | | Phenyl | 4-(N-Morpholinyl)-phenyl | | 580 nm |
| 2) | Benzo fusion* | | Phenyl | 4-(N-Morpholinyl)-phenyl | | 575 nm |

*The benzo fusion of the inventive compound 1) also has a methoxy substituent in the ortho position to the seven-membered ring bridge, and that of the inventive compound 2) a methyl substituent.

To measure the properties of the inventive photochromic dyes and of the prior art compound (see above), 500 ppm of each dye were dissolved in an acrylate monomer matrix and, after addition of a polymerization initiator, thermally polymerized with the aid of a temperature program. The transmission properties of the plastic lenses thus produced (thickness 2 mm) were subsequently analyzed to DIN EN ISO 8980-3.

The inventive compounds can be used in polymer materials or plastics articles of any kind and form for a multitude of end uses for which photochromic behavior is of significance. A dye according to the present invention or a mixture of such dyes can be used. For example, the inventive photochromic benzopyran dyes can be used in lenses, especially ophthalmic lenses, lenses for spectacles and goggles of all kinds, for example ski goggles, sunglasses, motorcycle goggles, visors of protective helmets, and the like. In addition, the inventive photochromic benzopyrans can also be used, for example, as sun protection in vehicles and living spaces, in the form of windows, protective screens, covers, roofs or the like.

To produce such photochromic articles, the inventive photochromic benzopyrans can be applied to a polymer material, such as an organic polymer material, or be embedded therein, by various processes described in the prior art as already specified in WO 99/15518.

A distinction can be drawn between bulk coloring and surface coloring processes. A bulk coloring process comprises, for example, the dissolution or dispersion of the photochromic compound or compounds according to the present invention in a polymer material, for example by the addition of the photochromic compound(s) to a monomeric material before polymerization is effected. A further means of producing a photochromic article is the penetration of the polymer material(s) with the photochromic compound(s) by immersing the polymer material into a hot solution of the photochromic dye(s) according to the present invention or else, for example, a thermal transfer process. The photochromic compound(s) may also be provided, for example, in the form of a separate layer between adjacent layers of the polymer material, for example as part of a polymeric film. In addition, it is also possible to apply the photochromic compound(s) as part of a coating present on the surface of the polymer material. The expression "penetration" in this context shall mean the migration of the photochromic compound(s) into the polymer material, for example by the solvent-supported transfer of the photochromic compound(s) into a polymer matrix, vapor phase transfer or other surface diffusion processes of this kind. Advantageously, it is possible to produce such photochromic articles, for example spectacle lenses, not only by means of customary bulk coloring, but also in the same way by means of surface coloring, it being possible to achieve a surprisingly relatively low migration tendency in the case of the latter variant. This is advantageous in particular in the case of subsequent finishing steps, since—for example in the case of an antireflection coating, as a result of the lesser back-diffusion under reduced pressure—layer detachment and similar defects are reduced drastically.

Overall, based on the inventive photochromic benzopyrans, it is possible to apply or to embed colorings, i.e. dyes, of any compatibility (compatible from a chemical point of view and in terms of color) to or into the polymer material, in order to satisfy both esthetic aspects and medical or fashion aspects. The specifically selected dye(s) may accordingly vary depending on the intended effects and requirements.

Figure 2:
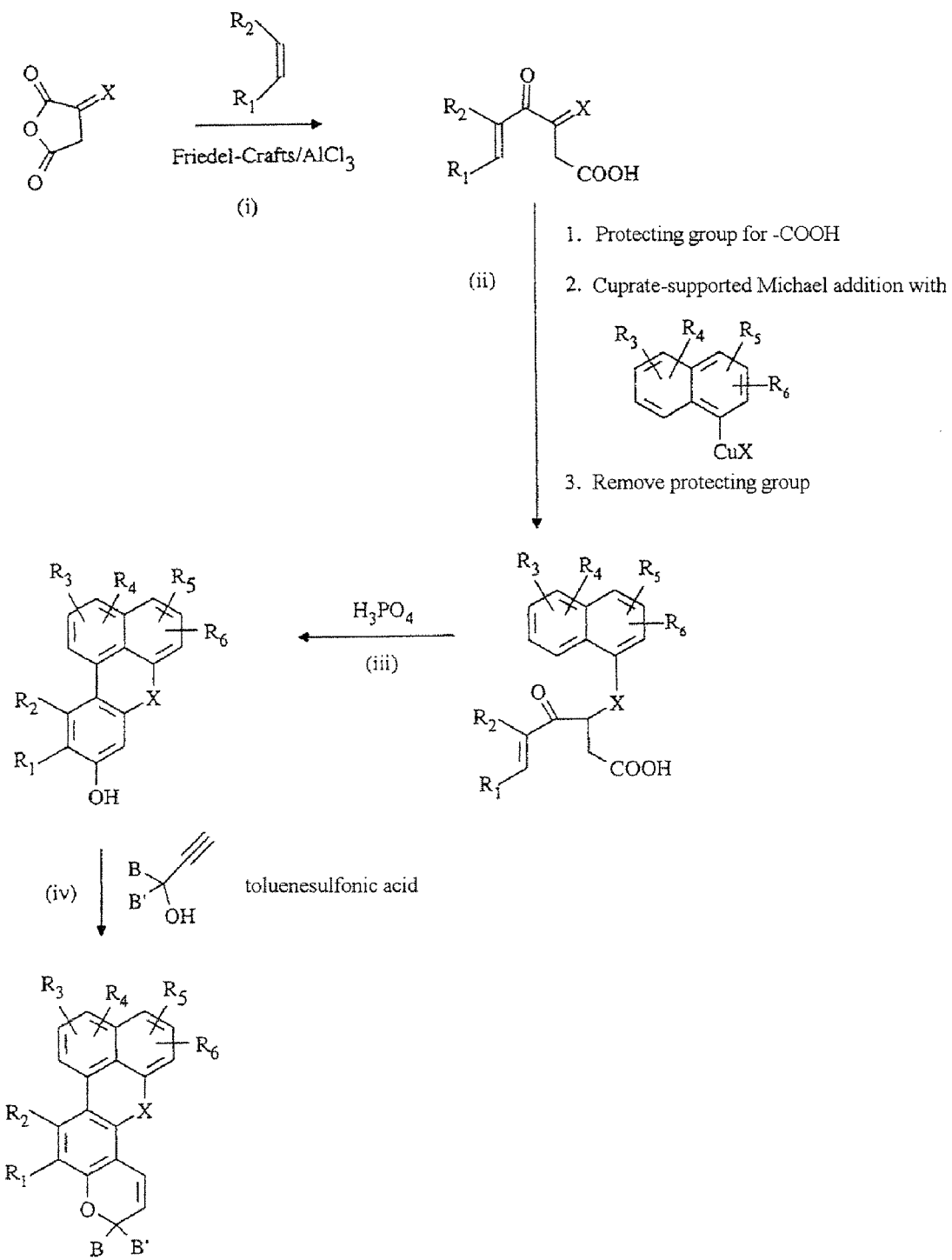
FIG. 2: Synthesis scheme of the inventive compound.

The inventive photochromic compounds can be prepared according to the illustrative synthesis scheme which follows, as shown in FIG. 2.

Corresponding succinic anhydride derivatives are subjected in a first step to a Friedel-Crafts reaction with suitably substituted 1,2-ethylenes (step (i)). The —COOH group of the resulting intermediate is subsequently protected and this intermediate is subjected to a Michael addition with correspondingly substituted naphthalene derivatives (step (ii)). After removal of the carboxylic acid protecting group, correspondingly substituted intermediates are formed via intramolecular cyclization by means of phosphoric acid (step (iii)). Subsequently, these substituted intermediates are reacted with suitably substituted 2-propyn-1-ol derivatives in step (iv) to give the inventive compounds.

The invention claimed is:
1. Photochromic benzopyrans with the general formula (I):

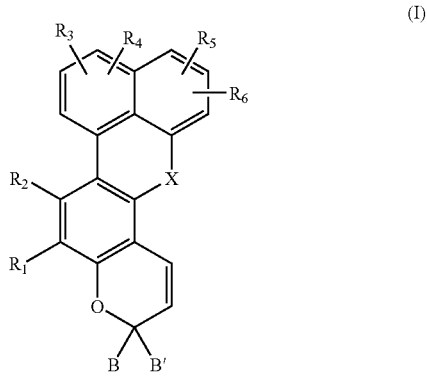

in which
the $R_1$, $R_2$, $R_3$, $R_4$, $R_5$ and $R_6$ radicals are each independently a substituent selected from the group α consisting of a hydrogen atom, a $(C_1\text{-}C_6)$-alkyl radical, a $(C_1\text{-}C_6)$-thioalkyl radical, a $(C_3\text{-}C_7)$-cycloalkyl radical which may have one or more heteroatoms, for example O or S, a $(C_1\text{-}C_6)$-alkoxy radical, a hydroxyl group, a trifluoromethyl group, bromine, chlorine, fluorine, an un-, mono- or disubstituted phenyl, phenoxy, benzyl, benzyloxy, naphthyl or naphthoxy radical, where the substituents may in turn be selected from the group α;

or the $R_1$ and $R_2$ or $R_3$ and $R_4$ or $R_4$ and $R_5$ or $R_5$ and $R_6$ radicals each independently form an -A-$(CH_2)_k$-D- or -A-$(C(CH_3)_2)_k$-D- group bonded to the aromatic ring, where k=1 or 2, where A and D are each independently selected from oxygen, sulfur, $CH_2$, $C(CH_3)_2$ or $C(C_6H_5)_2$, and where a benzo ring may in turn be fused to this -A-$(CH_2)_k$-D- group;

or the $R_1$ and $R_2$ or $R_3$ and $R_4$ or $R_5$ and $R_6$ radicals are each independently an unsubstituted, mono- or disubstituted, fused benzo, pyrido, naphtho, benzofuro or benzothieno ring, the substituents of which may be selected from the group α;

X is a mono- or diatomic bridge,
where X in the case of a monoatomic bridge is selected from O and $CR_7R_8$,
where the $R_7$ and $R_8$ radicals are each independently selected from the group α, or including the spiro carbon atom are a 3- to 8-membered carbo- or heteromonocyclic ring which optionally bears one or more substituents from the group α and to which one to three aromatic or heteroaromatic ring systems may be fused, where the ring system(s) is/are independently selected from the group β consisting of benzene, naphthalene, phenanthrene, pyridine, quinoline, furan, thiophene, pyrrole, benzofuran, benzothiophene, indole and carbazole, which may in turn be substituted by one or more substituents selected from the group α, or including the spiro carbon atom are a 7- to 12-membered carbobicyclic ring or a 7- to 12-membered carbotricyclic ring which may in turn have one, two, three or four substituents selected from the group α, or where X, in the case of a diatomic bridge, is formed from the —Y—Z— moiety, where Y and Z are each independently selected from O, $CR_9R_{10}$ and $CR_{11}R_{12}$, where the $R_9$ to $R_{12}$ radicals are each independently selected from the group α, or $R_9$ and $R_{10}$ or $R_{11}$ and $R_{12}$ including the spiro carbon atom are a 3- to 8-membered carbo- or heteromonocyclic ring which optionally bears one or more substituents from the group α and to which one to three aromatic or heteroaromatic ring systems may be fused, where the ring system(s) is/are independently selected from the group β consisting of benzene, naphthalene, phenanthrene, pyridine, quinoline, furan, thiophene, pyrrole, benzofuran, benzothiophene, indole and carbazole, which may in turn be substituted by one or more substituents selected from the group α, or $R_9$ and $R_{10}$ or $R_{11}$ and $R_{12}$ including the spiro carbon atom are a 7- to 12-membered, carbobicyclic ring or a 7- to 12-membered carbotricyclic ring which may in turn have one, two, three or four substituents selected from the group α;

or Y and Z are joined to one another via a radical in each case to form a 4- to 8-membered carbocyclic ring, where the ring members may each independently bear one or more substituents selected from the group α;

with the proviso that, in the case of a diatomic bridge, only a maximum of one carbobicyclic or carbotricyclic system is present, and that Y and Z are not both O; and B and B' are each independently selected from one of the following groups a), b) and c):

a) mono-, di- and trisubstituted aryl radicals, where the aryl radical is phenyl, naphthyl or phenanthryl;

b) unsubstituted, mono- and disubstituted heteroaryl radicals, where the heteroaryl radical is pyridyl, furanyl, benzofuranyl, thienyl, benzothienyl, 1,2,3,4-tetrahydrocarbazolylor julolidinyl;

where the substituents of the aryl or heteroaryl radicals in a) and b) are those selected from the above-defined group α or from the group χ consisting of hydroxyl, 2-phenylethenyl un-, mono- or disubstituted on the phenyl ring, (phenylimino)methylene un-, mono- or disubstituted on the phenyl ring, (phenylmethylene) imino un-, mono- or disubstituted on the phenyl ring, amino, mono-$(C_1-C_6)$-alkylamino, di-$(C_1-C_6)$-alkylamino, mono- and diphenylamino un-, mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, un-, mono- or disubstituted phenothiazinyl, un-, mono- or disubstituted phenoxazinyl, un-, mono- or disubstituted 1,2,3,4-tetrahydroquinolinyl, un-, mono- or disubstituted 2,3-dihydro-1,4-benzoxazinyl, un-, mono- or disubstituted 1,2,3,4-tetrahydroisoquinolinyl, un-, mono- or disubstituted phenazinyl, un-, mono- or disubstituted carbazolyl, un-, mono- or disubstituted 1,2,3,4-tetrahydrocarbazolyl and un-, mono- or disubstituted 10,11-dihydrodibenzo[b,f]azepinyl, where the substituent(s) may each independently in turn be selected from $(C_1-C_6)$-alkyl, $(C_1-C_6)$-alkoxy, bromine, chlorine and fluorine;

or where two directly adjacent substituents are a U—$(CV_2)_p$—W— moiety where p=1, 2 or 3, V may be hydrogen, $CH_3$ or $C_6H_5$, and U and W may each independently be oxygen, sulfur, N—$(C_1-C_6)$-alkyl, N—$C_6H_5$, $CH_2$, $C(CH_3)_2$ or $C(C_6H_5)_2$, where two or more adjacent carbon atoms in this U—$(CV_2)_p$—W— moiety may each independently also be part of a benzo ring system fused thereto, which may in each case in turn have one or more substituents selected from the group α or the group χ;

or c) B and B' together with the adjacent carbon atom of the pyran ring form an un-, mono- or disubstituted 9,10-dihydroanthracene, fluorene, thioxanthene, xanthene, benzo[b]fluorene, 5H-dibenzo[a,d]cycloheptene or dibenzosuberone radical, or a saturated hydrocarbon radical which is $(C_3-C_{12})$-spiromonocyclic, $(C_7-C_{12})$-spirobicyclic or $(C_7-C_{12})$-spirotricyclic, where the substituents of the unsaturated cycles may each independently be selected from the group α or the group χ.

2. Photochromic benzopyrans according to claim 1 which have the following general formulae (II) and (III):

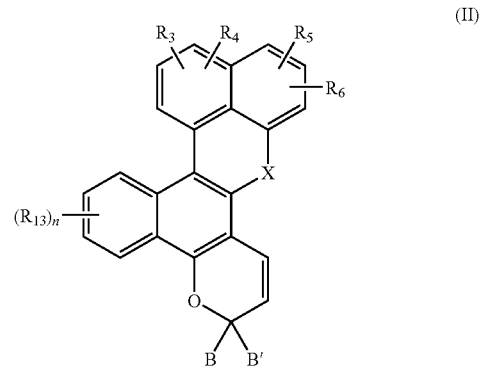

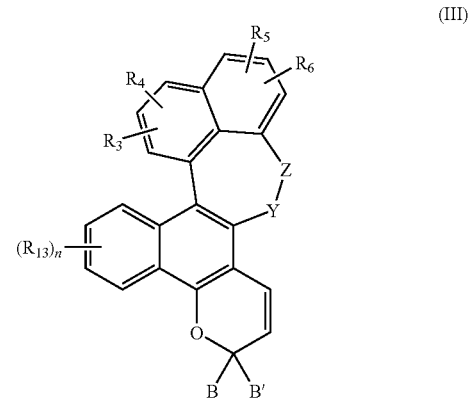

in which X is O or $CR_7R_8$, Y and Z are each as defined above, and B, B', $R_3$, $R_4$, $R_5$, $R_6$, $R_7$ and $R_8$ are each as defined above, $R_{13}$ is selected from the group α and n is 0, 1, 2, 3 or 4.

3. Photochromic benzopyrans according to claim 1, where X is a monoatomic bridge selected from O, $CH_2$ or $CMe_2$.

4. Photochromic benzopyrans according to claim 1, where X is a diatomic bridge Y—Z selected from $CH_2$-$CH_2$, O—$CH_2$, $CH_2$—O or a benzo fusion.

5. Photochromic benzopyrans according to claim 1, where the $R_7$ and $R_8$ or $R_9$ and $R_{10}$ or $R_{11}$ and $R_{12}$ radicals including the spiro carbon atom are a 5- to 8-membered carbocyclic ring which may in turn have one, two, three or four substituents selected from the group α, where one to three benzo rings may be fused to the carbocyclic ring, which may in turn have one or two substituents selected from the group α.

6. Photochromic benzopyrans according to claim 1, where the $C_7$-$C_{12}$-spirobicyclic systems specified for $R_7$ to $R_{12}$ and B and B' are selected from norbornane, norbornene, 2,5- norbornadiene, norcarane and pinane, and the spirotricyclic system is selected from adamantane, where the aforementioned spiro systems may each in turn have one, two, three or four substituents selected from the group α.

7. Photochromic benzopyrans according to claim 1, where B and B' are each independently selected from group a).

8. Photochromic benzopyrans according to claim 2, where X is a monoatomic bridge selected from O, $CH_2$ or $CMe_2$.

9. Photochromic benzopyrans according to claim 2, where X is a diatomic bridge Y—Z selected from $CH_2$—$CH_2$, O—$CH_2$, $CH_2$—O or a benzo fusion.

10. Photochromic benzopyrans according to claim 2, where the $R_7$ and $R_8$ or $R_9$ and $R_{10}$ or $R_{11}$ and $R_{12}$ radicals including the spiro carbon atom are a 5- to 8-membered carbocyclic ring which may in turn have one, two, three or four substituents selected from the group α, where one to three benzo rings may be fused to the carbocyclic ring, which may in turn have one or two substituents selected from the group α.

11. A process of making an article, comprising applying to or embedding in a polymer material the photochromic benzopyrans according to claim 2.

12. A process according to claim 11, wherein the article is an ophthalmic lens.

13. A process of making an article, comprising applying to or embedding in a polymer material the photochromic benzopyrans according to claim 1.

14. A process according to claim 13, wherein the article is an ophthalmic lens.

* * * * *